United States Patent [19]

Beers

[11] 4,080,167
[45] Mar. 21, 1978

[54] APPARATUS FOR ASEPTICIZING SOFT CONTACT LENSES AT HIGH TEMPERATURE

[76] Inventor: Charles J. Beers, 1818 Cortez Rd. W., No. 101C, Bradenton, Fla. 33507

[21] Appl. No.: 705,465

[22] Filed: Oct. 22, 1976

[51] Int. Cl.² .......................... A61L 3/00; A61L 3/02
[52] U.S. Cl. .......................................... 21/86; 21/99; 21/105; 219/385; 219/432
[58] Field of Search ....................... 21/93–99, 21/82 R, 82 H, 85, 86, 89, 103, 105, 100; 219/385, 387, 432, 439, 401

[56] References Cited

U.S. PATENT DOCUMENTS

| 2,275,672 | 3/1942 | Bruni et al. | 21/85 |
| 2,294,087 | 8/1942 | Johnson | 21/89 |
| 2,879,367 | 3/1959 | McLean | 219/385 |
| 3,247,360 | 4/1966 | Ponder | 219/321 |
| 3,271,860 | 1/1966 | Burton | 21/105 |
| 3,437,423 | 4/1969 | Mondiadis | 21/105 |
| 3,571,563 | 3/1971 | Shulz | 21/103 |
| 3,584,196 | 6/1971 | Kurokawa | 219/432 |
| 3,801,278 | 4/1974 | Wagner et al. | 21/86 |
| 3,879,171 | 4/1975 | Tulis | 21/82 R |

FOREIGN PATENT DOCUMENTS

| 561,060 | 9/1932 | Germany | 21/103 |

*Primary Examiner*—Barry S. Richman
*Assistant Examiner*—Bradley R. Garris

[57] ABSTRACT

Apparatus for the asepticizing by heat of soft contact lenses, wherein the lenses are placed in an autoclave which through automatic action raises and maintains them above a temperature level and for a duration to kill the germs, bacteria, and viruses which might otherwise be harmful to the wearer of such lenses.

1 Claim, 4 Drawing Figures

APPARATUS FOR ASEPTICIZING SOFT CONTACT LENSES AT HIGH TEMPERATURE

BACKGROUND OF THE INVENTION

1. Field of the Invention

This invention relates to the field of optics. More particularly to the use of soft contact lenses to improve human sight and most particularly to an apparatus for killing germs, bacteria, and viruses which might contaminate such lenses.

2. Description of the Prior Art

Soft contact lenses are made from a hydrophilic material. Hence, they absorb liquids, particularly human tears. This, plus their being held in contact with the eye and thus being sustained at the external temperature of the eye makes them a potential source of infection by absorption and growth of pathogenic microorganisms. The lenses should be made clean and aseptic between wearing intervals.

Presently, users of soft contact lenses asepticise them by one of two methods. One method is to immerse them in an antiseptic solution; hydrogen peroxide, for example. After soaking in the antiseptic, the lenses are repeatedly immersed in sterile water or saline solutions until enough of the antiseptic is removed from the lenses as to pose only a minor hazard to the human eye. A second method generally proceeds as follows: the soft contact lenses are immersed in a saline solution inside a container. The container is then sealed against fluid flow. The container is next immersed in steam from water boiling in an unsealed vessel. The temperature of the steam on the outside of the lens-holding container is generally at or below 212° F., depending on elevation. The walls of the sealed container act as insulating barriers with respect to heat flow. Thus, the temperature of the lenses and saline solution inside the container rises at a moderate and ever-decreasing rate from ambient (the temperature of the lenses, saline solution, and container at the start of the asepticising cycle) towards the temperature of the steam or boiling water. The presently-used devices which create the steam on the outside of the container are designed and constructed to shut themselves off automatically before the temperature inside the lens-holding container reaches 212° F. The walls of both the lens-holding container and of the steam-generating vessel are only fair (not good) insulating barriers to heat flow. Thus, after the steam-generating unit has been automatically shut off, heat flows out from the lenses and saline solution. The temperature of the lenses decreases at a moderate though ever-decreasing rate towards ambient. This method of asepticising soft contact lenses subjects them to a temperature of less than 212° F. as a peak temperature. Also the lenses are maintained at temperatures near this peak temperature for only a short period of time. When used at places of high elevation above sea level and/or conditions of low ambient temperature, this method of asepticising soft contact lenses fails to subject them to a high enough temperature, sustained for a sufficient duration, to kill many of the pathogenic microorganisms with which they may become contaminated. Also, since these present devices which use heat do so by boiling water in an unsealed vessel, they provide an opportunity for injury to anyone who may be contacted by the boiling water or steam during their operation.

SUMMARY OF THE INVENTION

This invention relates generally to an improved apparatus for aseptisising soft contact lenses at high temperature. More particularly, this invention provides for the placing of one or a single pair of soft contact lenses plus a saline solution in a compact container which is thermally insulated and capable of being sealed to withstand pressure differences of ten or more pounds per square inch between the inside and the outside (an autoclave). The autoclave is provided with an electrical resistance heater on the inside. The saline solution and lenses are heated in the autoclave; this causes a portion of the saline solution to change from a liquid to a vapor, which is not allowed to escape. Thus, the temperature and pressure inside the autoclave both rise until they reach predetermined levels. At the predetermined levels, the heat is shut off by automatically disconnecting the electrical resistance heater from its electrical energy source. The insulation of the autoclave is sufficiently good that the heat flow out of the autoclave takes place slowly enough to insure that the lenses remain above a specified temperature level for a specified time duration, thus killing most or all pathogenic microorganisms which might infect the wearer of the lenses.

The invention is so designed that the autoclave may not be opened during the time that the lenses and saline solution inside it are at temperatures above those harmful to most humans.

Therefore, from the foregoing, it should be understood that objects of this invention include the asepticising of soft contact lenses by raising them to or above a minimum predetermined temperature, this temperature being above the temperature at which water boils in an open vessel; to raise them to or above this same minimum predetermined temperature for each asepticising cycle, independent of the elevation above sea level or the ambient temperature at the time and place where the asepticising is done; to hold them above a predetermined temperature level for a predetermined minimum time duration; to do this in such a way as to avoid the possibility of burning or scalding or otherwise injuring the user or anyone else.

DESCRIPTION OF AN ILLUSTRATIVE EMBODIMENT

Figure 1:
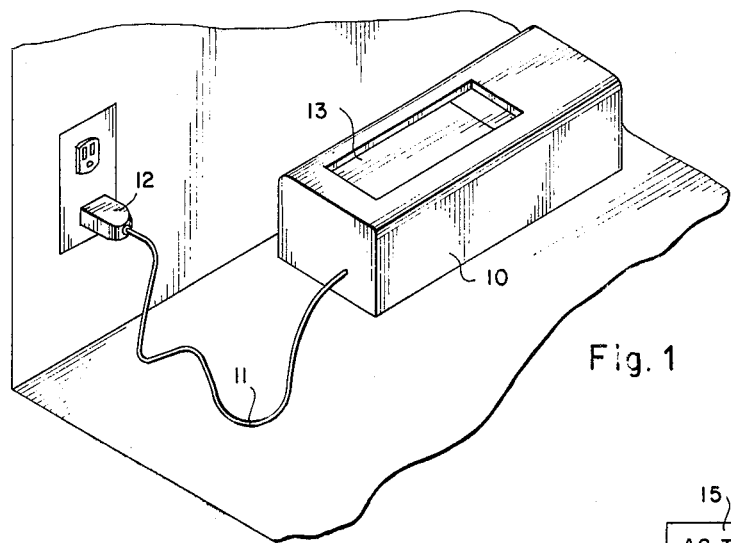
FIG. 1 is a perspective view of an illustrative configuration of the apparatus as it would appear during use.

Referring to FIG. 1, a power unit 10 is shown as it would appear during operation. An electrical cord 11 is shown with its plug 12 inserted into a standard 110–130 volt AC electrical outlet. An autoclave 13 is shown inserted in the power unit 10. The preferred embodiment includes a lamp 14 which emits light during the asepticising cycle.

Figure 2:
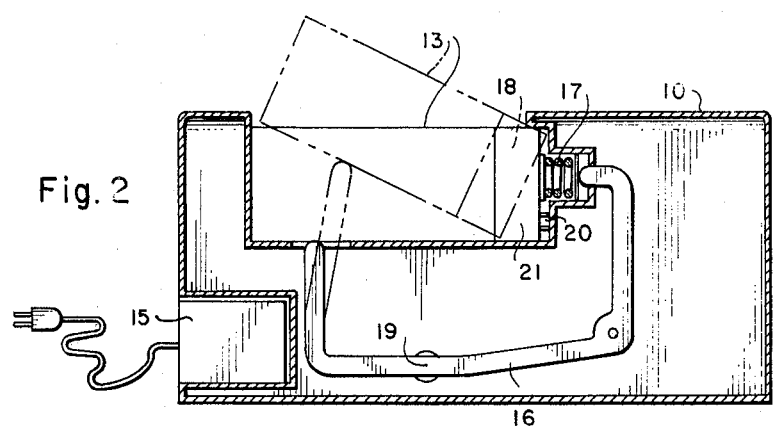
FIG. 2 is a cross-sectional view of an illustrative power unit, showing an autoclave being inserted at the start of an automatic asepticising cycle.

FIG. 2, an interior view, shows the electrical cord 11 connected to an AC to DC converter 15. The preferred embodiment includes a step-down transformer in this converter 15 so that the other electrical components of the apparatus operate on low voltage DC rather than high voltage electrical energy. Referring further to FIG. 2, it is seen that the act of inserting the autoclave 13 into the power unit 10 depresses a pivoted arm 16, thus compressing a spring 17. This spring 17, when compressed, provides external pressure against the cover 18 of the autoclave 13 when it is under internal pressure during an asepticising cycle, thus keeping the autoclave 13 sealed. When the autoclave 13 has been completely inserted into the power unit 10, a latch 19 engages the pivoted arm 16; this prevents the compressed spring 17 from ejecting the autoclave 13 until the cycle is complete. Referring further to this FIG. 2, it can be seen that the mating parts of electrical connectors 20 on the power unit 10 and other mating parts of electrical connectors 21 on the autoclave 13 are joined when the autoclave 13 is fully inserted into the power unit 10.

Figure 3:
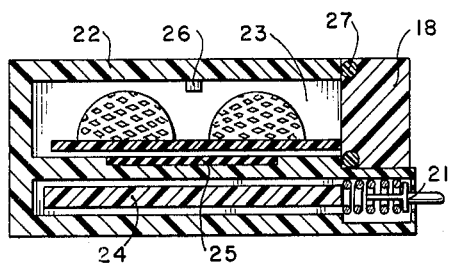
FIG. 3 is a cross-sectional view of an illustrative autoclave.

FIG. 3 shows an autoclave in cross section. The walls 22 surrounding the cavity 23 into which the user places soft contact lenses are insulated, thus providing a thermal barrier to heat flowing from the cavity 23 to the outside of the autoclave. The preferred embodiment of these walls 22 is a sandwich construction with the plastic skins bonded to a plastic foam interior. In the preferred embodiment, the outside skin would be ABS or similar, to provide rigidity, scuff resistance, easy cleaning, and good appearance. The interior skin would be a plastic approved for contact with soft contact lenses. In the preferred embodiment, the foam in these walls 22 would have a closed cell characteristic with average cells being less than one-fortieth of an inch in diameter. Alternate embodiments would have walls 22 of multi-layered insulating construction. One such multi-layered embodiment would have alternating layers of aluminum and asbestos as the insulating core of s sandwich with plastic interior and exterior skins. The walls 22 are insulated well enough so that when the lenses and saline solution in the cavity 23 are raised to a temperature of 236° F. or greater, these contents of the autoclave will lose heat only at such a low rate that with no heat or other energy or material added to the interior of the autoclave, they will remain above 212° F. for not less than five minutes, with no change of phase of the contents. This FIG. 3 also shows an electronic module, 24, an electrical resistance heater 25, and a temperature sensor 26 installed in the autoclave. By means of these, plus the insulating character of the walls 22, it is to be understood that when the autoclave is joined to an electrical energy source through the electrical connector mating parts 21, the contents of the autoclave may be raised to a high temperature; further, that this temperature may be sensed and regulated by switching logic in the electronic module 24. Referring further to FIG. 3, a seal 27 is shown where the cover 18 and the walls 22 of the autoclave meet. This seal keeps the saline solution in when the autoclave is used as a carrying case or container for the soft contact lenses and also to contain both the liquid and vapor phases of the saline solution during an asepticising cycle. It is to be understood that when the autoclave is not attached to the power unit, the autoclave cover 18 is held closed by friction or a latch or spring-loaded detent mechanism or similar means.

Figure 4:
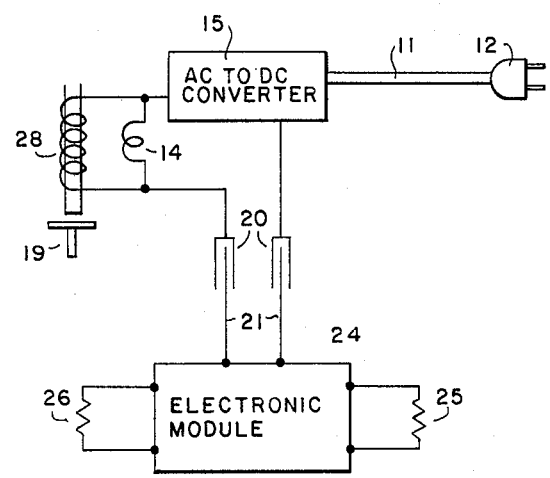
FIG. 4 is a diagram of the electrical hookup of an illustrative embodiment of the invention.

Referring to FIG. 4, which is an electrical hookup diagram of an illustrative embodiment of the invention, it is seen that the logic of the electronic module 24 determines the operating characteristics of the apparatus. The preferred embodiment uses a solid state electronic sensing and switching logic to automatically control the apparatus throughout each asepticising cycle. An illustrative algorithm for this electronic module 24 is as follows:

If the temperature as sensed the sensor 26 is less than 120° F., the module 24 switches on current to the heater 25 and allows current to flow through the coil 28. Since the lamp 14 is hooked up electrically in parallel with the coil 28 the lamp 14 will also remain lighted.

If the sensed temperature is greater than 120° F., but equal to or less than 150° F., and if the heater 25 has been switched on so that current is flowing through it, the electronic module 24 takes no action.

If the sensed temperature is greater than 120° F., but equal to or less than 150° F., and the heater 25 has been switched off so that no current is flowing through it, the electronic module 24 switches off the current which flows through the coil 28 and also resets itself for a new asepticising cycle.

If the sensed temperature is greater than 150° F., and less than 236° F., the electronic module 24 takes no action.

If the sensed temperature is equal to or greater than 236° F., the electronic module 24 switches off the heater 25 so no current flows through it.

The logic set which starts an asepticising cycle is that of sensing a temperature of 120° F. or less. This not only holds the autoclave in the power unit, but also turns on the heater, thus causing the interior temperature to rise. The logic set which terminates a cycle is that of sensing a temperature of greater than 120° F. and less than or equal to 150° F. while simultaneously sensing that the heater is switched off. When this logic set is satisfied and the electronic module shuts off current through the coil, the latch is retracted by a spring. The autoclave is then pushed part way out of the power unit by the action of the pivoted arm - spring combination. This same section disengages the electrical connection between the autoclave and the power unit.

Although the illustrative embodiment employs an electronic module physically located in the autoclave, alternate embodiments may have the module located in the power unit or partly in the autoclave and partly in the power unit.

Although the illustrative embodiment calls for automatic actions to be triggered by temperatures of 120°, 150°, and 236° F., alternate embodiments may employ other temperatures as trigger points.

Although the illustrative embodiment employs a recess in the top of the power unit into which the autoclave is inserted, alternate embodiments may employ recesses in the side or end of the power unit; the autoclave may even merely attached to the power unit; whatever the location and means of attachment, this invention provides a means of preventing the autoclave from being opened while it is at high temperature or pressure.

Indeed, it is to be understood that the forms of the invention herein shown and described are to be taken as illustrative embodiments only of the same, and that various changes in the shape, size, and arrangement of parts as well as various procedural changes may be resorted to without departing from the spirit of the invention as defined in the following claims.

I claim as my invention:

1. Apparatus for ascepticising soft contact lenses comprising:

an autoclave having a chamber for said contact lenses, said chamber being defined by insulated walls, one of said walls comprising a sealable inlet means;

said autoclave further having an electrical resistance heater for heating said chamber and means for sensing the temperature in said chamber;

said apparatus further comprising a power unit for supplying electrical energy to said autoclave and having an indent therein for housing said autoclave;

said indent having a spring means resiliently engaging said inlet means and thereby sealing said inlet means;

and said power unit further having means operatively connected to said spring means for automatically ejecting said autoclave from said indent and for simultaneously disconnecting the electrical energy of said power unit from said autoclave at the end of an ascepticising cycle, said ejecting and disconnecting means including latch means for preventing actuation thereof prior to completion of the ascepticising cycle.

* * * * *